US00PP17554P2

(12) United States Plant Patent
Hofmann

(10) Patent No.: US PP17,554 P2
(45) Date of Patent: Apr. 3, 2007

(54) **NEW GUINEA *IMPATIENS* PLANT NAMED 'FISCO CHER'**

(50) Latin Name: *Impatiens hawkeri*
Varietal Denomination: Fisco Cher

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 11/241,394

(22) Filed: Sep. 30, 2005

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of New Guinea *Impatiens* plant named 'Fisco Cher', characterized by its relatively compact, outwardly spreading and uniformly mounded plant habit; rounded growth habit; freely branching and freely flowering habit; dark green-colored foliage; large dark cherry red-colored flowers; and flowers that are positioned above or beyond the foliage.

1 Drawing Sheet

Botanical designation: *Impatiens hawkeri.*
Cultivar denomination: 'Fisco Cher'.

BACKGROUND OF THE INVENTION

The present Invention relates to a new and distinct cultivar of New Guinea *Impatiens* plant, botanically known as *Impatiens hawkeri,* and hereinafter referred to by the name 'Fisco Cher'.

The new *Impatiens* is a product of a planned breeding program conducted by the Inventor in Hillscheid, Germany and Galdar, Canary Islands, Spain. The objective of the breeding program is to develop new compact *Impatiens* cultivars that flower relatively early and have attractive flower coloration.

The new *Impatiens* originated from a cross-pollination made by the Inventor during the summer of 2001 in Hillscheid, Germany of the *Impatiens hawkeri* cultivar Kinoc, disclosed in U.S. Plant Pat. No. 10,433, as the female, or seed, parent with a proprietary selection of *Impatiens hawkeri* identified as code number K01-8608-69, not patented, as the male, or pollen, parent. The cultivar Fisco Cher was discovered and selected by the Inventor as a flowering plant within the progeny of the stated cross-pollination in a controlled environment in Galdar, Canary Islands, Spain in April, 2002.

Asexual reproduction of the new cultivar by terminal cuttings in Galdar, Canary Islands, Spain since September, 2002, has shown that the unique features of this new *Impatiens* are stable and reproduced true to type in successive generations.

SUMMARY OF THE INVENTION

The following traits have been repeatedly observed and are determined to be the unique characteristics of 'Fisco Cher'. These characteristics in combination distinguish 'Fisco Cher' as a new and distinct *Impatiens* cultivar:

1. Relatively compact, outwardly spreading and uniformly mounded plant habit; rounded growth habit.
2. Freely branching and freely flowering habit.

3. Dark green-colored foliage.
4. Large dark cherry red-colored flowers.
5. Flowers that are positioned above or beyond the foliage.

Plants of the new *Impatiens* can be compared to plants of the female parent, the cultivar Kinoc. In side-by-side comparisons conducted by the Inventor in Hillscheid, Germany, plants of the new *Impatiens* differed from plants of the cultivar Kinoc in the following characteristics:

1. Plants of the new *Impatiens* were more compact than plants of the cultivar Kinoc.
2. Plants of the new *Impatiens* and the cultivar Kinoc differed in flower color as plants of the cultivar Kinoc had red purple-colored flowers.

Plants of the new *Impatiens* can be compared to plants of the male parent selection. In side-by-side comparisons conducted by the Inventor in Hillscheid, Germany, plants of the new *Impatiens* differed from plants of the male parent selection in the following characteristics:

1. Plants of the new *Impatiens* were slightly taller than plants of the male parent selection.
2. Plants of the new *Impatiens* had darker green-colored foliage than plants of the male parent selection.
3. Plants of the new *Impatiens* and the male parent selection flowered earlier than plants of the male parent selection.
4. Plants of the new *Impatiens* had smaller flowers than plants of the male parent selection.
5. Plants of the new *Impatiens* had darker-colored flowers than plants of the male parent selection.

Plants of the new *Impatiens* can also be compared to plants of the cultivar Fisimp 171, disclosed in U.S. Plant Pat. No. 13,703. In side-by-side comparisons conducted by the Inventor in Hillscheid, Germany, plants of the new *Impatiens* differed from plants of the cultivar Fisimp 171 in the following characteristics:

1. Plants of the new *Impatiens* were smaller than plants of the cultivar Fisimp 171.
2. Plants of the new *Impatiens* had smaller and darker green-colored leaves than plants of the cultivar Fisimp 171.

3. Plants of the new *Impatiens* flowered earlier than plants of the cultivar Fisimp 171.
4. Plants of the new *Impatiens* had smaller flowers than plants of the cultivar Fisimp 171.
5. Plants of the new *Impatiens* had darker cherry red-colored flowers than plants of the cultivar Fisimp 171.
6. Plants of the new *Impatiens* had shorter peduncles than plants of the cultivar Fisimp 171.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Fisco Cher' grown in a container.

DETAILED BOTANICAL DESCRIPTION

The cultivar Fisco Cher has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers and the aforementioned photograph and following observations and measurements were taken about three months later. During the production of the plants, day temperatures were about 16° C. to 20° C. and night temperatures were about 16° C. In the following description, color references are made to The Royal Horticultural Society Colour Chart, 2001 Edition, except where general terms of ordinary dictionary significance are used.

Botanical classification: *Impatiens hawkeri* cultivar Fisco Cher.

Parentage:

*Female parent.*—*Impatiens hawkeri* cultivar Kinoc, disclosed in U.S. Plant Pat. No. 10,433.

*Male parent.*—Proprietary selection of *Impatiens hawkeri* identified as code number K01-8608-69, not patented.

Propagation:

*Type cutting.*—Terminal tip cuttings.

*Time to initiate roots.*—Summer: About 10 days at 24° C. Winter: About 12 to 15 days at 21° C.

*Time to produce a rooted cutting.*—Summer: About 15 days at 24° C. Winter: About 18 to 20 days at 21° C.

*Root description.*—Fine, fibrous; 158D in color.

*Rooting habit.*—Freely branching.

Plant description:

*General appearance.*—Relatively compact, outwardly spreading and uniformly mounded plant growth habit; low and rounded growth habit; freely branching habit; bushy appearance; freely flowering. Low to moderate vigor.

*Crop time.*—From a rooted cutting, about nine weeks are required to produce finished flowering plants in 12-cm containers.

*Plant height.*—About 10.3 cm.

*Plant diameter or spread.*—About 21.2 cm.

*Lateral branches.*—Quantity per plant: About seven. Length: About 6 cm to 8 cm. Diameter: About 4 mm to 7 mm. Internode length: About 1.5 cm to 2.5 cm. Texture: Smooth, glabrous. Color: 185A; towards the apex, 183A.

*Foliage description.*—Arrangement: Primarily in whorls. Length: About 11 cm. Width: About 4 cm. Shape: Narrowly elliptic. Apex: Acuminate. Base: Acute. Margin: Serrulate with ciliation. Texture, upper and lower surfaces: Smooth, slightly rugose; glabrous. Color: Developing foliage, upper surface: 137A. Developing foliage, lower surface: 139C. Fully expanded foliage, upper surface: 139A. Fully expanded foliage, lower surface: 139C. Venation, upper surface: 147C; towards the base, 53D. Venation, lower surface: 53B. Petiole: Length: About 1.5 cm. Diameter: About 3 mm. Texture, upper and lower surfaces: Smooth, glabrous. Color, upper surface: 181B. Color, lower surface: 53B.

Flower description:

*Flower type and flowering habit.*—Single, large and rounded flowers. Freely and continuously flowering; usually about six to nine flowers and flower buds per lateral branch. Flowers positioned above or beyond the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Early flowering habit; plants begin flowering about eight to nine weeks after planting.

*Flower buds.*—Length: About 2.1 cm. Diameter: About 1.5 cm. Shape: Ovoid. Color: 46B.

*Flower length.*—About 6.8 cm.

*Flower width.*—About 6.3 cm.

*Flower depth.*—About 1.2 cm.

*Petals.*—Quantity: Five per flower, imbricate. Length: Banner petals: About 2.9 cm. Lateral and base petals: About 2.9 cm. Width: Banner petal: About 4.5 cm. Lateral petals: About 3.1 cm. Base petals: About 3.7 cm. Shape: Cordate. Apex: Moderately lobed; emarginate. Base: Attenuate. Margin: Entire. Aspect: Nearly flat to slightly concave. Texture, upper and lower surfaces: Smooth; satiny. Color: When opening, upper surface: 46B. When opening, lower surface: Between 46B and 46C. Fully opened, upper surface: Between 46B and N57A; towards the base, N66B; faint streak on banner petal, N66B. Fully opened, lower surface: 53C to 53D.

*Spur.*—Quantity: One per flower. Length: About 5 cm. Diameter: At apex: About 0.5 mm. At flower: About 3 mm. Aspect: Curved. Texture: Smooth, glabrous. Color: 53B.

*Peduncles.*—Length: About 5 cm. Diameter: About 2 mm. Texture: Smooth, glabrous. Strength: Strong, flexible. Color: 185A.

*Reproductive organs.*—Androecium: Stamen number: Five fused at anthers, hooded; filaments free. Anther length: About 6 mm. Anther shape: Obovate. Anther color: 58B. Pollen amount: Moderate. Pollen color: 8D. Gynoecium: Pistil quantity: One per flower. Pistil length: About 5 mm to 6 mm. Stigma color: 12D. Style color: 12D. Ovary: Five-celled. Ovary color: 143B.

*Seed/fruit.*—Seed and fruit development has not been observed.

Disease/pest resistance: Plants of the new *Impatiens* have not been observed to be resistant to pathogens and pests common to *Impatiens*.

Low temperature tolerance: Plants of the new *Impatiens* have been observed to tolerate night temperatures of 5° C. with 10° C. day temperatures.

It is claimed:

1. A new and distinct cultivar of New Guinea *Impatiens* plant named 'Fisco Cher', as illustrated and described.

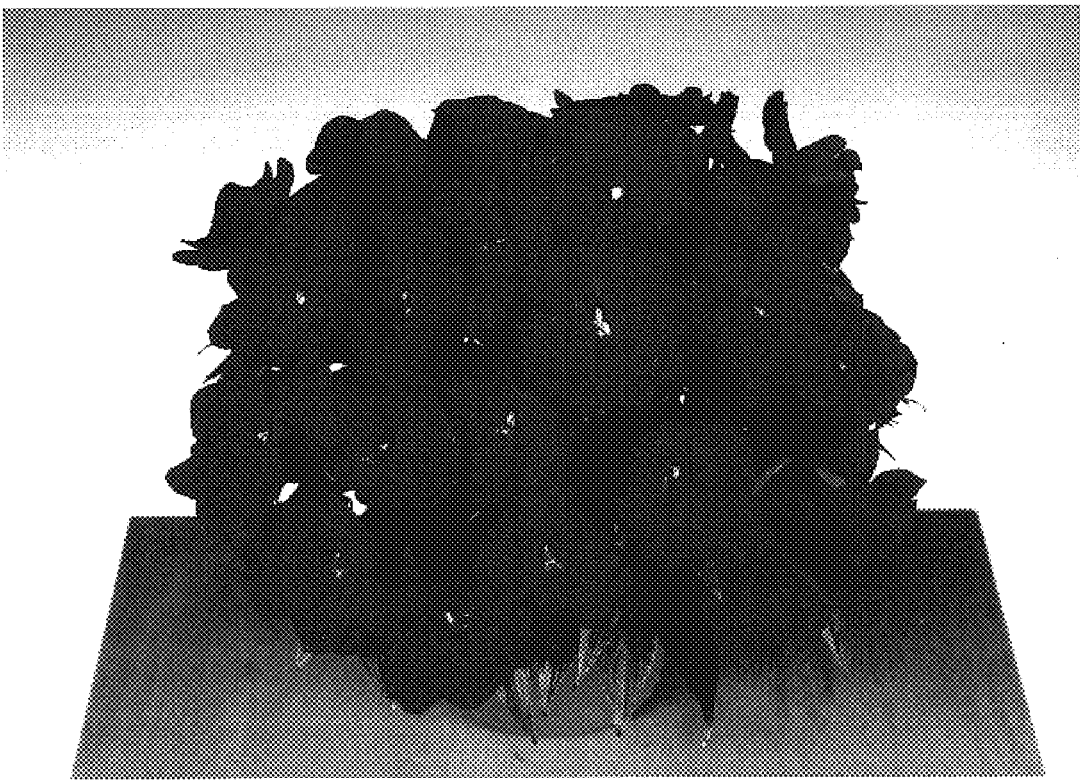

* * * * *